United States Patent [19]

Feyen et al.

[11] Patent Number: 5,145,837
[45] Date of Patent: Sep. 8, 1992

[54] TREATMENT OF ARTHRITIS

[75] Inventors: Jean H. M. Feyen, Oberwil; Janos Pless, Basel, both of Switzerland

[73] Assignee: Sandoz Ltd., Basel, Switzerland

[21] Appl. No.: 715,937

[22] Filed: Jun. 14, 1991

Related U.S. Application Data

[63] Continuation of Ser. No. 360,503, Jun. 2, 1989, abandoned.

[30] Foreign Application Priority Data

Jun. 6, 1988 [GB] United Kingdom ............... 88133392

[51] Int. Cl.⁵ ............... C07K 7/26; A61K 37/02
[52] U.S. Cl. .................. 514/16; 530/311; 530/328; 530/317; 514/8; 514/9
[58] Field of Search ............ 514/8, 9, 11, 12, 16; 530/311, 328, 317

[56] References Cited

U.S. PATENT DOCUMENTS 3,970,571 6/1976 Olson et al. ............... 430/110

FOREIGN PATENT DOCUMENTS 0187622 7/1986 European Pat. Off. .
59-078364 5/1984 Japan .
61-258268 11/1986 Japan .
63-008652 1/1988 Japan .
2206352 1/1989 United Kingdom .

Primary Examiner—Lesier L. Lee
Assistant Examiner—A. M. Davenport
Attorney, Agent, or Firm—Gerald D. Sharkin; Robert S. Honor; Thomas O. McGovern

[57] ABSTRACT

Somatostatin analogues and derivatives in free form or in pharmaceutically acceptable salt or complex form are useful for treating degenerative and inflammatory processes in bone or catilage, e.g. arthritic conditions or diseases.

11 Claims, No Drawings

TREATMENT OF ARTHRITIS

This is a continuation of application Ser. No. 07/360,503, filed Jun. 2, 1989 and now abandoned.

The present invention relates to a new use, in particular a new use for the compound group comprising somatostatin analogues and derivatives, in free form or in pharmaceutically acceptable salt or complex form, said compound group being referred to hereinafter collectively as COMPOUNDS OF THE INVENTION.

Somatostatin is a tetradecapeptide incorporating a cyclic dodecapeptide having the structure

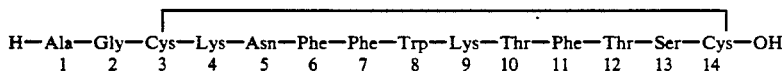

and has the properties of inhibiting the release of growth hormone, insulin and glucagon and reducing gastric secretions.

By the terms "somatostatin analogue or derivative" as used herein is meant any straight-chain or cyclic polypeptide derived from that of the naturally occurring tetradecapeptide somatostatin wherein one or more amino acid units have been omitted and/or replaced by one or more other amino radical(s) and/or wherein one or more functional groups have been replaced by one or more other functional groups and/or one or more groups have been replaced by one or several other isosteric groups. The terms "analogue or derivative" also include the corresponding peptides bearing a sugar residue. In general, the term covers all modified derivatives of a biologically active peptide which exhibit a qualitatively similar effect to that of the unmodified somatostatin peptide, e.g. they bind to somatostatin receptors and inhibit secretion of GH.

Cyclic, bridge cyclic and straight-chain somatostatin analogues or derivatives are known and have been described together with processes for their production e.g. in U.S. Pat. No. 4,310,518 and 4,235,886, in European Patent Specifications EP-A-1295; 29,310; 29,579; 63,308; 70,021; 215,171; 203,031; 214,872; 143,307; 298,732; 277,419 and in Belgian Patent Specification BE-A-900,089.

When the COMPOUNDS OF THE INVENTION bear a sugar residue, this is preferably coupled to an amino group thereof by a coupling other than a direct N-glycosidic bond, preferably to a N-terminal amino group and/or to at least one amino group present in a peptide side chain, more preferably to a N-terminal amino group. Such compounds and their preparation are disclosed e.g. in WO 88/02756.

Preferred compounds of the invention are:

A. Compounds of formulae I to III

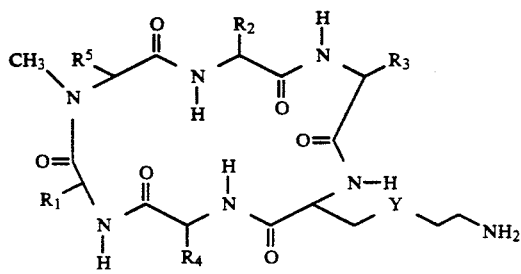

I

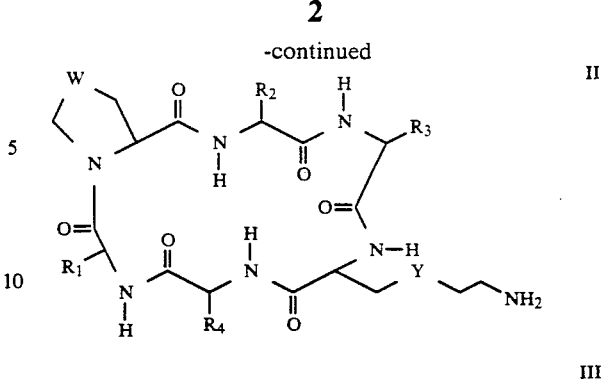

II

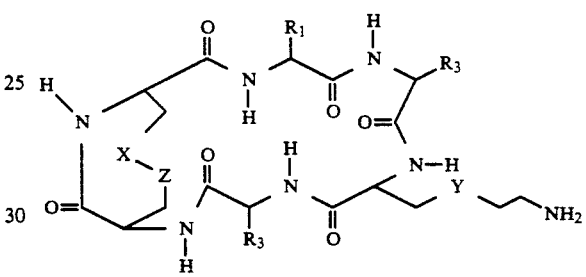

III wherein

W is S or $(CH_2)_s$ where s is 0, 1 or 2;

one of X and Z is S and the other is S or $CH_2$;

Y is S or $(CH_2)_t$ where t is 0, 1 or 2;

each of $R_1$ and $R_2$ independently of the other, is $C_{1-5}$ alkyl, benzyl, benzyl having one or two $C_{1-5}$ alkyl, halogen, hydroxy, amino, nitro, and/or $C_{1-5}$ alkoxy substituents, or $C_{1-5}$ alkyl substituted with a 5- or 6-membered heterocyclic ring;

$R_3$ is 3-indolylmethyl, either unsubstituted or having $C_{1-5}$ alkyl, $C_{1-5}$ alkoxy or halogen substitution;

$R_4$ is $C_{1-5}$ alkyl, $C_{1-5}$ hydroxyalkyl, benzyl, carboxy-($C_{1-5}$ alkyl), amino ($C_{1-5}$ alkyl) or benzyl having a $C_{1-5}$ alkyl, halogen, hydroxy, amino, nitro and/or $C_{1-5}$ alkoxy substituent;

$R_5$ is $C_{1-5}$ alkyl, benzyl, or benzyl having a $C_{1-5}$ alkyl, halogen, hydroxy, amino, nitro, and/or $C_{1-5}$ alkoxy substituent.

Examples of $C_{1-5}$ alkyl groups are methyl, ethyl, propyl, iso-propyl, butyl, sec-butyl and pentyl; examples of $C_{1-5}$ alkoxy groups are methoxy, ethoxy, propoxy, isopropoxy, butoxy, tert-butoxy, and pentoxy; halogens are fluorine, chlorine, bromine, or iodine: and the term "5- or 6-membered heterocyclic ring" represents such rings with one or two oxygen, nitrogen and/or suphur heteroatoms, e.g. imidazole, furan, thiazole, pyrazole and pyridine.

In the compounds of Formulae I, II and III, there are several asymmetric centres which lead to the existence of optical isomers for such compounds. For each of the asymmetric centres of the various amino acids which make up these cyclic hexapeptides, both the D and L configurations are included.

The following are representative cyclic hexapeptide analogues of somatostatin of Formulae I, II and III:

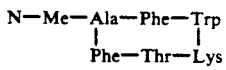

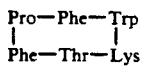

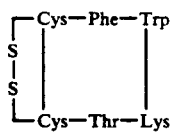

Preferred Formula I compounds are:
1) Cyclo-(N-Me-Ala-Tyr-D-Trp-Lys-Thr-Phe)
2) Cyclo-(N-Me-Ala-Phe-D-Trp-Lys-Thr-Phe)
3) Cyclo-(N-Me-Ala-Phe-L-Trp-Lys-Thr-Phe)
4) Cyclo-(N-Me-Ala-Phe-D-Trp-Lys-Thr-p-Cl-Phe)
5) Cyclo-(N-Me-Ala-Phe-D-5-F-Trp-Lys-Thr-Phe)
6) Cyclo-(N-Me-Ala-Phe-L-5-F-Trp-Lys-Thr-Phe)
7) Cyclo-(N-Me-Ala-Phe-D-Trp-Lys-Ser-Phe)
8) Cyclo-(N-Me-Ala-Tyr-D-Trp-Lys-Val-Phe)
9) Cyclo-(N-Me-Ala-Tyr-D-Trp-Lys-Val-Trp)
10) Cyclo-(N-Me-Ala-Tyr-L-Trp-Lys-Val-Phe)
11) Cyclo-(Ser-Ala-N-Me-Phe-His-D-Trp-Lys)

Preferred Formula II compounds are:
12) Cyclo-(Pro-Tyr-D-Trp-Lys-Thr-Phe)
13) Cyclo-(Pro-Phe-D-Trp-Lys-Thr-Phe)
14) Cyclo-(Pro-Phe-L-Trp-Lys-Thr-Phe)
15) Cyclo-(Pro-Phe-D-Trp-Lys-Thr-p-Cl-Phe)
16) Cyclo-(Pro-Phe-D-5-F-Trp-Lys-Thr-Phe)
17) Cyclo-(Pro-Phe-L-5-F-Trp-Lys-Thr-Phe)
18) Cyclo-(Pro-Phe-D-Trp-Lys-Ser-Phe)

Preferred Formula III compounds are:

19) Cyclo-(Cys — Cys—Tyr-D-Trp—Lys—Thr)

20) Cyclo-(Cys — Cys—Tyr-D-Trp—Lys—Val)

21) Cyclo-(Cys — Cys—Tyr-L-Trp—Lys—Val)

22) Cyclo-(Cys — Cys—Phe-D-Trp—Lys—Thr)

23) Cyclo-(Cys — Cys—Phe-L-Trp—Lys—Thr)

24) Cyclo-(Cys — Cys—His-D-Trp—Lys—Thr)

25) Cyclo-(Cys — Cys—His-D-Trp—Lys—Val)

26) Cyclo-(Cys — Cys—Aha—Phe-D-Trp—Lys—Thr).

B. Compounds of formula IV

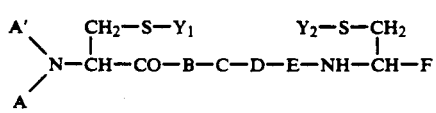

wherein

A is $C_{1-12}$ alkyl, $C_{7-10}$ phenylalkyl or a group of formula RCO—, whereby
  i) R is hydrogen, $C_{1-11}$ alkyl, phenyl or $C_{7-10}$ phenylalkyl, or
  ii) RCO-is
    a) an L- or D-phenylalanine residue optionally ring-substituted by halogen, $NO_2$, $NH_2$, OH, $C_{1-3}$ alkyl and/or $C_{1-3}$ alkoxy
    b) the residue of a natural or a synthetic α-amino acid other than defined under a) above or of a corresponding D-amino acid, or
    c) a dipeptide residue in which the individual amino acid residues are the same or different and are selected from those defined under a) and/or b) above,
    the α-amino group of amino acid residues a) and b) and the N-terminal amino group of dipeptide residues c) being optionally mono-or di-$C_{1-12}$ alkylated, A' is hydrogen or, when A is $C_{1-12}$ alkyl or $C_{7-10}$ phenylalkyl, also $C_{1-12}$ alkyl or $C_{7-10}$ phenylalkyl, $Y_1$ and $Y_2$ represent together a direct bond or each of $Y_1$ and $Y_2$ is independently hydrogen or a radical of formulae (1) to (5)

$$-CO-NHR_c \qquad (3)$$

$$-CO-NH-CH-COOR_e \atop \qquad\quad |\atop \qquad\quad R_d \qquad (4)$$

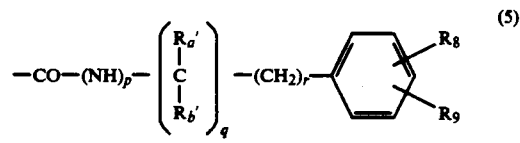

wherein
$R_a$ is methyl or ethyl
$R_b$ is hydrogen, methyl or ethyl
m is a whole number from 1 to 4
n is a whole number from 1 to 5
$R_c$ is $(C_{1-6})$alkyl
$R_d$ represents the substituent attached to the α-carbon atom of a natural or synthetic α-amino acid (including hydrogen)
$R_e$ is $(C_{1-5})$alkyl
$R_a'$ and $R_b'$ are independently hydrogen, methyl or ethyl,
$R_8$ and $R_9$ are independently hydrogen, halogen, $(C_{1-3})$alkyl or $(C_{1-3})$alkoxy,
p is 0 or 1,
q is 0 or 1, and
r is 0, 1 or 2,
B is —Phe— optionally ring-substituted by halogen, $NO_2$, $NH_2$, OH, $C_{1-3}$alkyl and/or $C_{1-3}$alkoxy, or 3-(2-naphthyl)-alanine
C is (L)-Trp- or (D)-Trp- optionally α-N-methylated and optionally benzene-ring-substituted by halogen, $NO_2$, $NH_2$, OH, $C_{1-3}$ alkyl and/or $C_{1-3}$ alkoxy D is Lys, Lys in which the side chain contains O or S in β-position, γF-Lys, δF-Lys or Orn, optionally α-N-methylated, or a 4-aminocyclohexylAla or 4-aminocyclohexylGly residue E is Thr, Ser, Val, Phe, Tyr, Ile or an aminoisobutyric or aminobutyric acid residue F is

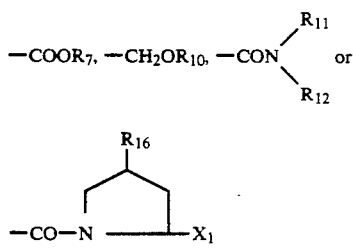

wherein $R_7$ is hydrogen or $C_{1-3}$alkyl, $R_{10}$ is hydrogen or the residue of a physiologically acceptable, physiologically hydrolysable ester, $R_{11}$ is hydrogen, $C_{1-3}$alkyl, phenyl or $C_{7-10}$phenylalkyl, $R_{12}$ is hydrogen, $C_{1-3}$alkyl or a group of formula-$CH(R_{13})$—$X_1$, $R_{13}$ is $CH_2OH$, —$(CH_2)_2$—OH, —$(CH_2)_3$—OH, or —$CH(CH_3)OH$ or represents the substituent attached to the α-carbon atom of a natural or synthetic α-amino acid (including hydrogen) and $X_1$ is a group of formula —$COOR_7$, —$CH_2OR_{10}$ or

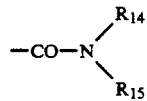

wherein $R_7$ and $R_{10}$ have the meanings given above, $R_{14}$ is hydrogen or $C_{1-3}$alkyl and $R_{15}$ is hydrogen, $C_{1-3}$alkyl, phenyl or $C_{7-10}$phenylalkyl, and $R_{16}$ is hydrogen or hydroxy, with the proviso that when $R_{12}$ is —$CH(R_{13})$—$X_1$ then $R_{11}$ is hydrogen or methyl, wherein the residues B, D and E have the L-configuration, and the residues in the 2- and 7-position and any residues $Y_1$ 4) and $Y_2$ 4) each independently have the (L)- or (D)-configuration, in free form or in pharmaceutically acceptable salt or complex form.

In the compounds of formula IV, the following significances are preferred either individually or in any combination or sub-combination:

1. A is $C_{7-10}$ phenylalkyl, especially phenethyl, or a group of formula RCO. Preferably A is a group of formula RCO.

1.1. Preferably R is $C_{1-11}$ alkyl or $C_{7-10}$ phenylalkyl, especially $C_{7-10}$ phenylalkyl, more especially phenethyl, or RCO has the meanings a), b) or c).

1.2. When RCO has the meanings a), b) or c), the α-amino group of amino acid residues a) and b) and the N-terminal amino group of dipeptide residues c) is preferably non-alkylated or mono-$C_{1-12}$ alkylated, especially —$C_{1-8}$ alkylated, more especially -methylated. Most preferably the N-terminal is non-alkylated.

1.3. When RCO has the meaning a) this is preferably a') an L- or D-phenylalanine or -tyrosine residue optionally mono-N-$C_{1-12}$ alkylated. More preferably a') is an L- or D-phenylalanine residue or an L- or D-N-($C_{1-8}$-alkyl)-phenylalanine residue. Most preferably a') is a D-phenylalanine or D-N-($C_{1-8}$ alkyl)-phenylalanine residue, especially a D-phenylalanine or D-(N-methyl)-phenylalanine residue.

1.4. When RCO has the meaning b) or c) the defined residue is preferably lipophilic. Preferred residues b) are thus b') α-amino acid residues having a hydrocarbon side chain, e.g. alkyl with 3, preferably 4, or more C atoms, e.g. up to 7 C-atoms, naphthyl-methyl or heteroaryl, e.g. 3-(2- or 1-naphthyl)-alanine residue or tryptophane residue, said residues having the L- or D-configuration, and preferred residues c) are dipeptide residues in which the individual amino acid residues are the same or different and are selected from those defined under a') and b') above.

Example of a residue c) is e.g. 3-(2-naphthyl)-alanine residue.

1.5. Most preferably RCO has the meaning a) especially the meaning a').

2. B is B', where B' is Phe or Tyr.

3. C is C', where C' is (D)Trp.

4. D is D', where D' is Lys, MeLys or Lys(ε-Me), especially Lys.

5. E is E', where E' is the residue of a natural α-amino acid, for example Val or Thr, especially Thr.

6. F is F', where F' is a group of formula

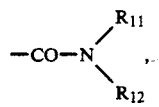

especially a group of formula

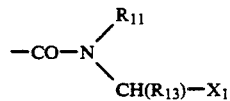

(in which case $R_{11}$=H or $CH_3$). In the latter case the moiety —$CH(R_{13})$—$X_1$ preferably has the L-configuration.

6.1. $R_{11}$ is preferably hydrogen.

6.2. As the substituent attached to the α-carbon atom of a natural amino acid (i.e. of formula $H_2N$—$CH(R_{1-3})$—COOH), $R_{13}$ is preferably —$CH_2OH$, —$CH(CH_3)$—OH, isobutyl or butyl, or $R_{13}$ is —$(CH_2)_2$—OH or —$(CH_2)_3$—OH. It is especially —$CH_2OH$ or —$CH(CH_3)OH$.

6.3. $X_1$ is preferably a group of formula

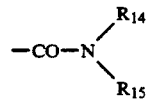

or —$CH_2$—$OR_{10}$, especially of formula —$CH_2$—$OR_{10}$ and $R_{10}$ is preferably hydrogen or has the meaning given under 7 below. Most preferably it is hydrogen.

7. As the residue of a physiologically acceptable, physiologically hydrolysable ester $R_{10}$ is preferably HCO, $C_{2-12}$ alkylcarbonyl, $C_{8-12}$ phenylalkylcarbonyl or benzoyl.

8. Preferably the residues in the 2- and 7-positions have the L-configuration.

9. Preferably $Y_1$ and $Y_2$ together represent a direct bond.

Preferred compounds of formula IV are for example:

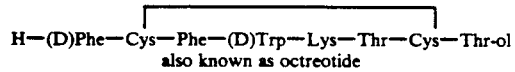
also known as octreotide

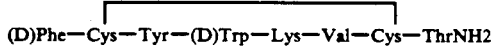

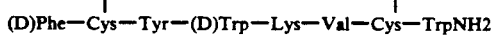

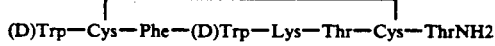

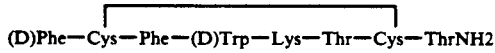
β-Naphthyl-

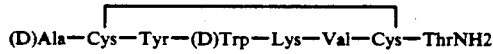

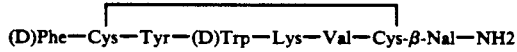

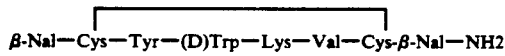

A most preferred compound of formula IV is the compound IVa

Suitable derivatives bearing at least one sugar residue are e.g. compounds of formula IV including the compound octreotide bearing a sugar residue preparable by an Amadori or Heyns rearrangement from a natural or a synthetically accessible mono-, di- or oligosaccharide e.g. as disclosed in WO 88/02756, the contents of which being incorporated herein by reference.

Preferred sugar somatostatin derivatives are the compounds of formula IV which have a sugar residue on the N-terminal amino group, e.g. a residue of formula

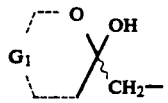

which is the deoxy residue of a ketose, e.g. a radical obtainable by means of an Amadori rearrangement from a natural or synthetically accessible mono-, di- or oligosaccharide, or a residue of formula

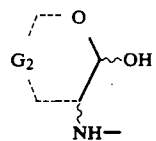

which is the deoxy residue of an aldose, e.g. a radical obtainable by means of a Heyns rearrangement from a natural or a synthetically accessible mono-, di- or oligoketose, or a residue of formula

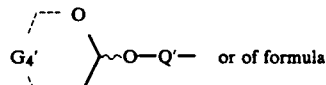 or of formula

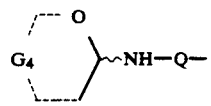

which are each independently a sugar residue and linked to the N-terminal amino group by a coupling group Q or Q', e.g. the radical of a dicarboxylic acid or $C_bH_{2b}$-CO-radical wherein b is 1 to 6.

A particularly preferred compound is $N^\alpha$-[α-glucosyl(1-4)-deoxy-fructosyl]-

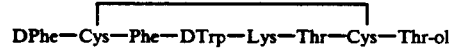

(referred to as compound of formula IVc).

C. Compounds of formulae V to IX

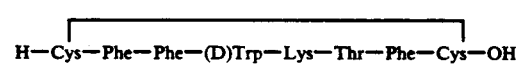   V

[see Vale et al., Metabolism, 27, Supp. 1, 139, (1978)]

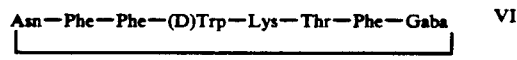   VI

[see European Patent Publication No. 1295 and Application No. 78 100 994.9]

   VII

[see R. F. Nutt et al. Klin. Wochenschr. (1986) 64 (Suppl. VII) 71–73.

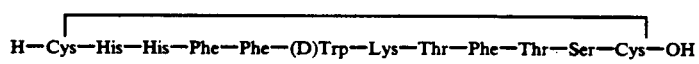   VIII (see EP-A-200,188)

Cyclo-(DTrp-Lys-Val-Phe-NMeAla-Tyr)   IX (see EP-A-70,021)

The contents of all the above publications including the specific compounds are specifically incorporated herein by reference.

The compounds of the invention may exist e.g. in free form, salt form or in the form of complexes thereof. Acid addition salts may be formed with e.g. organic acids, polymeric acids and inorganic acids. Such acid addition salt forms include e.g. the hydrochlorides and acetates. Complexes are e.g. formed from compounds of the invention on addition of inorganic substances, e.g. inorganic salts or hydroxides such as Ca- and Zn-salts, and/or an addition of polymeric organic substances.

Somatostatin analogues and derivatives are mainly disclosed as having an inhibitory effect on growth hormone, glucagon and insulin secretion.

In accordance with the present invention it has now been found that COMPOUNDS OF THE INVENTION have a beneficial effect on arthritis.

In accordance with the particular findings of the invention, the present invention provides, in a first aspect:

1. A method of treating degenerative and inflammatory processes in bone or cartilage in a subject in need thereof, which method comprises administering to said subject an effective amount of a COMPOUND OF THE INVENTION. 1.1. A method of treating arthritic conditions or diseases in a subject in need thereof, which method comprises administering to said subject an effective amount of a COMPOUND OF THE INVENTION.

1.2. A method for the supportive or adjunct treatment of degenerative and inflammatory processes in bone or cartilage, e.g. treatment of arthritic conditions or diseases in a subject in need thereof, which comprises administering to said subject an effective amount of a COMPOUND OF THE INVENTION.

1.3. A method for treating degenerative and inflammatory processes in bone or cartilage, e.g. treating arthritic conditions or diseases in a subject in need of such a treatment which method comprises administering to said subject an effective amount of a) a COMPOUND OF THE INVENTION and b) a second drug substance, said second drug substance being a dopamine agonist, for example bromocriptine.

In a particular embodiment the invention provides a method as defined under 1 and 1.1. to 1.3. above for example for the treatment of rheumatic tissue and joint diseases, e.g. arthritis, rheumatoid arthritis, osteoarthritis, polychondritis, spondylarthropaties (e.g. ankylosing spondylitis, Reiter's syndrome, psoriatic arthritis, and enteropathic arthritis, arthritis in lupus erythematosus and vasculitic syndromes, or for the treatment of humoral hypercalcemia of malignancy.

As alternatives to the above the present invention also provides:

2. A COMPOUND OF THE INVENTION for use in any method as defined above;

3. A COMPOUND OF THE INVENTION for use in the manufacture of a pharmaceutical composition for use in any method as defined above;

4. A pharmaceutical composition for use in any method as defined above comprising a COMPOUND OF THE INVENTION together with one or more pharmaceutically acceptable diluents or carriers therefor.

5. A pharmaceutical composition for use in any method as defined above comprising a COMPOUND OF THE INVENTION and a dopamine agonist.

Utility of the COMPOUNDS OF THE INVENTION in treating diseases and conditions as hereinabove specified, may be demonstrated in standard pharmacological test methods as well as in clinic, for example in accordance with the methods hereinafter described.

1. INHIBITORY EFFECT ON PROSTAGLANDIN E2 PRODUCTION STIMULATED BY PTH

Organ cultures of mouse calvariae are first prepared according to the principles of U. L. Ivey, D. R. Wright, A. H. Tashjian, J. Clin. Invest. 58:1327 (1976) as follows:

Frontal and parietal bones are dissected from neonatal (5 to 6-day-old) mice (strain CD-1), split along the sagittal suture, and cultured in 2 ml of BGJ-medium containing 1 mg/ml bovine serum albumin, penicillin and streptomycin in 35 mm plastic tissue culture wells.

After the preculture period (24 hours), the medium is replaced with BGJ-medium supplemented with parathyroid hormone at $10^{-9}$M and the COMPOUND OF THE INVENTION at $10^{-6}$ to $10^{-8}$M.

The cells are cultured for another 48 hours. During the entire culture period, the multi-well dishes are shaken on a rocker platform (15 oscillations/min) in a humidified atmosphere of 5% $CO_2$ in air at 37° C. The calvaria-conditioned medium is harvested and placed at 4° C.

An aliquot of the medium is then assayed for prostaglandin $E_2$ using a standard radioimmunossay. Prostaglandin $E_2$ levels are reduced.

Representative results obtained with the compound IVa are as follows:

|  | Dose M | PGE$_2$ synthesis pg/ml |
|---|---|---|
| Control |  | 20 |
| PTH | $10^{-10}$ | 50 |
| PTH + Compound IVa | $10^{-10}$ $10^{-7}$ | 60 |
| PTH | $10^{-7}$ | 340 |
| PTH + Compound IVa | $10^{-9}$ $10^{-7}$ | 40 |
| Compound IVa | $10^{-7}$ | 85 |

As can be seen a total inhibition of PGE$_2$ synthesis is attained with compound IVa at $10^{-7}$M.

2. FREUND'S ADJUVANT ARTHRITIS TEST

The methodology is based on that of Pearson et al., Arthritis and Rheumatism 2, 400 (1959).

OFA or Wistar rats (♂ and ♀, 150 g) receive 0.1 ml mineral oil containing 0.6 mg lyophylised, heat-killed Mycobacterium smegmatis (LHMS) administered i.c. at the base of the tail or in the left hind paw. Administration of test substance, s.c. at varying dosage, commences immediately after injection of LHMS continuing through days 1 to 18 for determination of efficacy in the developing-arthritis model or from day 14 continuing through day 20 in the established-arthritis model. Swelling of the joints is measured by micro-caliper at the conclusion of the test. The ED$_{50}$ for test substance is taken as the dosage required to reduce swelling by 50% as compared with untreated controls.

The COMPOUNDS OF THE INVENTION, in particular the compound IVa, reduce arthritic reactions in the above test model as compared with control animals at dosages of from 0.1 to 500 μg/kg s.c.

3. INHIBITION OF DEGENERATIVE LESION FORMATION FOLLOWING PARTIAL MENISCECTOMY IN THE RABBIT

The test is effected according to the principles of R. W. Moskowitz, Arthritis and Rheumatism (1973) 16, 397. Degenerative lesions induced by partial meniscectomy resemble degenerative joint disease observed in osteoarthritis.

Anesthetized rabbits are subjected to a partial meniscectomy in the right knee as described in the above-mentioned article, and then allowed to move freely. The COMPOUNDS OF THE INVENTION are administered at from 0.1 µg to 500 µg/kg daily over 12 weeks and animals are then sacrificed. The operated knees are then examined for osteophyte-like spurs, pitting, ulcerative and other degenerative lesion formation.

In this test, COMPOUNDS OF THE INVENTION, in particular the compound IVa or IVc, inhibit formation of degenerative lesions induced by partial meniscectomy in the rabbit knee.

4. RHEUMATOID ARTHRITIS

4.1. CLINICAL TRIAL 1

Twenty patients either male or female, at least 18 years old, with active arthritis as defined by ARA (American Rheumatism Association) criteria, are submitted in a double-blind study.

Patients are included who have rheumatoid arthritis for at least 6 months prior to the initiation of the study. The patients exhibit at least 3 parameters of the followings:

a. More than 3 swollen joints
b. Duration of morning stiffness >45 minutes
c. Sedimentation rate >30 mm Hg (by Westergren)
d. More than 6 painful or tender joints
e. Grip strength abnormalities, males <175, females <125 mm Hg
f. Physician's global assessment of at least "3" on a scale of 1 to 5 upon entry.

Patients are taking a stable dose of gold, d-penicillamine or methotrexate for at least 3 months prior to the trial, and have continued active disease, including dysfunction and pain.

Preferably the trial excludes:

a. Patients with a history or presence of malignancy, serious active or recurrent infections, severe heart disease, severe respiratory disease or insulin dependent diabetes.
b. Patients who are ARA functional class IV
c. Patients who have received any investigational drug within one month prior to this study.
d. Patients requiring treatment with Imuran or total irradiation
e. Patients with clinically significant laboratory abnormalities that may interfere with assessment of safety and/or efficacy of the study drug.
f. Patients with any significant disease or postsurgical state of the liver, kidney, heart or gastrointestinal tract which will comprise absorption, metabolism or excretion of the compound.
g. Patients with a past or current history of alcohol or drug abuse.
h. Patients who have received drugs with a known potential for toxicity to a major organ system in the past 3 months.

Each patient is randomized to receive either a COMPOUND OF THE INVENTION or matching placebo for 8 weeks, followed by a 4 week washout.

At week 1, all patients randomized to the COMPOUND OF THE INVENTION receive initially 50 µg on days 1–4 and 100 µg on days 5–7. Patients responding to treatment of 100 µg of the COMPOUND OF THE INVENTION at the end of Week 1 remain on this dose until the end of the study (Week 8). The dose of the non-responders at the following weeks may be increased.

Patients may remain on stable doses of non-steroidal anti-inflammatory medications and/or prednisone during the course of the study; all efforts are made to continue the same medication, dosage and dosage schedule used at study entry.

Clinical efficacy and safety parameters are evaluated during this 12 week period, e.g. as follows:

a. ARA functional class (I-III)
b. Duration of morning stiffness on the day before evaluation
c. Grip strength (mm Hg)
d. Time to walk fifty feet (in seconds)
e. Button test (in seconds) using a standard button board, containing five buttons. With the button board buttoned, the patient is instructed to unbutton and then button the five buttons on the board using one hand only. Right and left hands are evaluated separately.
f. Global assessment of disease activity by the investigator on a five-point scale.
g. Results of the therapy as compared to Baseline Week 0 by the investigator an a five-point scale.
h. Pain/tenderness and swelling is scored on each joint.

During the course of the study, subjects receive a COMPOUND OF THE INVENTION, e.g. compound IVa or IVc, at dosages of from ca. 50 to ca. 500 µg s.c. or ca. 0.1 to ca. 10 mg p.o daily administered once or in divided dosages up to 4x daily.

Subjects receiving therapy in accordance with the invention, exhibit improvement in their rheumatoid arthritic conditions.

4.2. CLINICAL TRIAL 2

20 rheumatoid arthritis patients, who meet the following inclusion/exclusion criteria are treated for a six month period with a COMPOUND OF THE INVENTION and are seen monthly for six months after discontinuing the treatment.

Inclusion criteria:

a. Definite or classical progressive rheumatoid arthritis as defined by the ARA criteria
b. Functional Class I, II or III patients
c. Disease Progression stage I, II or III
d. Age 18 years or older
e. Onset of rheumatoid arthritis after age 16 years
f. Patient possesses active disease of the joints capable of response (joint shows evidence of active inflammation without loss of >50% range movement) to anti-arthritic drug treatment as follows:

i. Patient has six or more actively inflamed joints potentially responsive to therapy and meet 2 of the following criteria:
   Nine or more responsive joints tender on pressure
   Forty-five minutes or more of morning stiffness
   Westergren sedimentation rate of 28 mm/hr or more
ii. Patient has been treated unsuccessfully with nonsteroidal anti-inflammatory drugs and second line drugs.

Exclusion criteria:

a. Disease Progression stage IV
b. Functional Capacity class IV
c. Thrombocytopenia and/or leukopenia d. History or presence of malignancy
e. Chronic liver disease and/or significant renal disease
f. Diabetic patients
g. Patients who have received intra-articular injection of steroids in previous 4 weeks prior to initial assessment
h. Patients receiving first line drugs for less than 6 months
i. Patients currently receiving oral steroids in doses greater than 10 mg daily or for less than 4 weeks prior to the study
j. Concomitant administration of gold, D-penicillamine, anti-malarials or cytotoxin drugs.

Consenting eligible patients have baseline assessments. History and physical examination is performed at baseline and study termination. Rheumatological examinations as follows are carried out at baseline, monthly, at study termination, by the same observer and at a similar time each day to avoid diurnal variation in measurements:

Joint tenderness evaluation using the modified Ritchie Articular Index (Klinkhoff et al. J. Rheumatol. 15(3), 492–494, 1986), carried out preferably in the afternoon,
Patient's global assessment
Pain assessment
Clinician's global assessment of disease activity
Measurement of function status by the administration of the "Mactar" [P. Tugwell et al. J. Rheumatol. 14(3), 446–451, 1987] and the modified Health Assessment Questionnaire [J. F. Fries, Arthritis Rheum 23, 137–144, 1980]
Morning stiffness estimation
Weekly patient diary The observed differences between baseline and subsequent assessments are analyzed using appropriate statistics for paired data on means and proportions.

During the course of the trial, subjects receive a COMPOUND OF THE INVENTION, e.g. compound IVa or IVc, at dosages of from ca. 50 to ca. 500 μg s.c. or ca. 0.1 to 10 mg p.o. daily, administered once or in divided dosages.

Subjects receiving COMPOUND OF THE INVENTION in the above indicated dosages, e.g. a daily dose of from 100 to 450 μg of compound IVa s.c., exhibit improvement in condition after the 6 months treatment period.

Equivalent results may be obtained in trials performed in relation to other diseases and conditions hereinbefore specified (e.g. osteoarthritis . . . ) employing COMPOUNDS OF THE INVENTION, in particular compound IVa or IVc, at the same or equivalent dosage levels to those described above.

The appropriate dosage will vary depending upon, for example, the somatostatin analogue employed, the host, the mode of administration and the severity of the condition being treated. Doses may be in the range used to treat gastroenteropancreatic endocrine (GI) tumours such as vipomas, or acromegaly, to about 10 times that dose.

Thus for compound IVa GI tumours may be treated initially with 0.05 mg once or twice a day by subcutaneous injection. Dosage can be increased to 0.2 mg three times daily. For acromegaly daily doses of from 100 to 300 μg s.c. may be used. Compound IVa is tolerated at least to 1 mg.

In general, satisfactory results in animals are indicated to be obtained at daily dosages from about 0.5 μg/kg to about 1000 μg/kg animal body weight. In larger mammals, for example humans, as indicated daily dosage is in the range from about 25 μg to about 1000 μg of the COMPOUND OF THE INVENTION conveniently administered, for example, in divided doses up to four times a day or in sustained release form. COMPOUNDS OF THE INVENTION may be administered by any conventional route, in particular enterally, e.g. in the form of tablets or capsules, or preferably parenterally, e.g. in the form of injectable solutions or suspensions, e.g. s.c., i.m. or intra-articularly. Compound IVa is preferably administered parenterally in the form of an injectable formulation, e.g. based on lactic acid. Compound IVa is the preferred compound. It is indicated that it may be administered at daily dosages of from 50 μg to 1 mg s.c. The compound IVc (octreotide with a sugar residue) is preferably administered in an oral form, e.g. at a dosage of 2 μg to 20 mg p.o., preferably 300 to 5000 μg p.o.. Oral unit dosages may contain for example from about 0.5 μg to about 10 mg of compound IVc.

Where the COMPOUNDS OF THE INVENTION are administered in conjunction with, e.g. as an adjuvant to, a dopamine agonist, e.g. for the treatment of specific diseases or conditions as hereinabove specified, the dopamine agonists may be used for example in free base form or in pharmaceutically acceptable acid addition salt form, e.g. the hydrochloride, maleate or mesylate. The preferred dopamine agonist is bromocriptine, preferably employed as the mesylate.

The effect of combined administration of a COMPOUND OF THE INVENTION and a dopamine agonist may be demonstrated in standard pharmacological test methods, e.g. in arthritic rats (adjuvant arthritis) as compared with animals receiving placebo after a 14-day treatment period. In such a trial, the dopamine agonist, e.g. bromocriptine, may be administered in microencapsulated form e.g. as a single i.m. dose of 25 mg/kg providing sustained release for 14 days; the COMPOUND OF THE INVENTION may be administered by subcutaneous implantation of continuous osmotic pumps releasing 5 μg/kg/h for 14 days.

Dosages for the co-administered dopamine agonist will of course vary depending on the type of agonist employed, on the condition to be treated, the therapy desired and so forth. The dopamine agonist may be administered at daily doses used to lower prolactin levels. For example bromocriptine is administered at a daily dose of 5 mg p.o. twice a day.

The composition for use according to the invention may be prepared by bringing a COMPOUND OF THE INVENTION into intimate admixture with the pharmaceutically acceptable diluents or carriers and effecting formulation or presentation so as to provide for or permit convenient administration.

The following is illustrative of the preparation of compositions in accordance with the invention.

| 1. Ampoules | Concentration per ml | | | |
| --- | --- | --- | --- | --- |
| | Ex. 1 | Ex. 2 | Ex. 3. | Ex. 4 |
| A. Octreotide* | 0.05 mg | 0.1 mg | 0.2 mg | 0.5 mg |
| Mannitol | 45.0 mg | 45.0 mg | 45.0 mg | 45.0 mg |
| Lactic acid (88%) | 3.4 mg | 3.4 mg | 3.4 mg | 3.4 mg |
| Sodium hydrogeno-carbonate | to pH 4.2 | to pH 4.2 | to pH 4.2 | to pH 4.2 |

-continued

| Concentration per ml | | | | |
|---|---|---|---|---|
| Water (inject. grade) | to 1 ml | to 1 ml | to 1 ml | to 1 ml |
| Carbon dioxide | q.s. | q.s. | q.s. | q.s. |
| | | | Ex. 5 | |
| B. Octreotide* | | 0.2 mg | | |
| NaCl | | 7.5 mg | | |
| Lactic acid (88%) | | 3.4 mg | | |
| Sodium hydrogeno-carbonate | | to pH 4.2 | | |
| Water (injection grade) | | to 1 ml | | |
| Carbon dioxide | | q.s. | | |
| 2. Vials | | Ex. 6 | | |
| Octreotide* | | 0.2 mg | | |
| Mannitol | | 45.0 mg | | |
| Lactic acid (88%) | | 3.4 mg | | |
| Phenol | | 5.0 mg | | |
| Sodium hydrogeno-carbonate | | to pH 4.2 | | |
| Water (injection grade) | | to 1 ml | | |
| Carbon dioxide | | q.s. | | |

*given as the acetate peptide content 87 per cent.

The compositions are prepared by standard techniques, e.g. in charges of 50 liters to provide about 43 000 ampoules of 1 ml or 8400 vials under carbon dioxide gassing. The compositions are filtered (e.g. through 0.2 micron holes at 0.5 bar) and introduced in the ampoules or vials under aseptic conditions.

COMPOUNDS OF THE INVENTION are well tolerated at dosages required for use in accordance with the present invention. Pharmaceutically acceptable salt forms exhibit the same or similar levels of tolerability/activity as the free compounds.

What is claimed is:

1. A method of treating degenerative and inflammatory processes in bone or cartilage in a subject in need thereof, which comprises administering to said subject an effective amount of a somatostatin analogue or derivative the formula

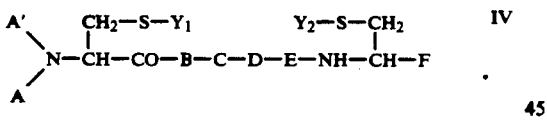

wherein
A is $C_{1-12}$ alkyl, $C_{7-10}$ phenylalkyl or a group of formula RCO-, whereby
  i) R is hydrogen, $C_{1-11}$ alkyl, phenyl or $C_{7-10}$ phenylalkyl, or
  ii) RCO-is
   a) an L- or D-phenylalanine residue optionally ring-substituted by halogen, $NO_2$, $NH_2$, OH, $C_{1-3}$ alkyl and/or $C_{1-3}$ alkoxy
   b) the residue of a natural or a synthetic α-amino acid other than defined under a) above or of a corresponding D-amino acid, or
   c) a dipeptide residue in which the individual amino acid residues are the same or different and are selected from those defined under a) and/or b) above,
the α-amino group of amino acid residues a) and b) and the N-terminal amino group of dipeptide residues c) being optionally mono-or di-$C_{1-12}$ alkylated,
A' is hydrogen or, when A is $C_{1-12}$ alkyl or $C_{7-10}$ phenylalkyl, also $C_{1-12}$ alkyl or $C_{7-10}$ phenylalkyl,
$Y_1$ and $Y_2$ represent together a direct bond or each of $Y_1$ and $Y_2$ is independently hydrogen or a radical of formulae (1) to (5)

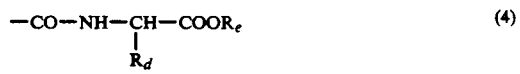

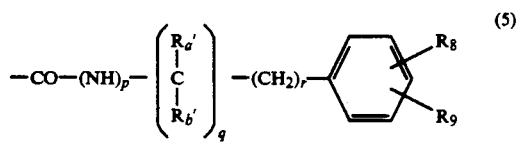

wherein
$R_a$ is methyl or ethyl
$R_b$ is hydrogen, methyl or ethyl
m is a whole number from 1 to 4
n is a whole number from 1 to 5
$R_c$ is $(C_{1-6})$alkyl
$R_d$ represents the substituent attached to the α-carbon atom of a natural or synthetic α-amino acid (including hydrogen)
$R_e$ is $(C_{1-5})$alkyl
$R_a'$ and $R_b'$ are independently hydrogen, methyl or ethyl,
$R_8$ and $R_9$ are independently hydrogen, halogen, $(C_{1-3})$alkyl or $(C_{1-3})$alkoxy,
p is 0 or 1,
q is 0 or 1, and
r is 0, 1 or 2,
B is —Phe— optionally ring-substituted by halogen, $NO_2$, $NH_2$, OH, $C_{1-3}$alkyl and/or $C_{1-3}$alkoxy, or 3-(2-naphthyl)-alanine
C is (L)-Trp- or (D)-Trp- optionally α-N-methylated and optionally benzene-ring-substituted by halogen, $NO_2$, $NH_2$, OH, $C_{1-3}$ alkyl and/or $C_{1-3}$ alkoxy
D is Lys, Lys in which the side chain contains O or S in β-position, γF-Lys, δF-Lys or Orn, optionally α-N-methylated, or a 4-aminocyclohexylAla or 4-aminocyclohexylGly residue
E is Thr, Ser, Val, Phe, Tyr, Ile or an aminoisobutyric or aminobutyric acid residue
F is

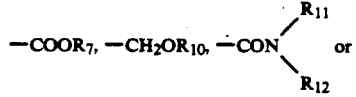

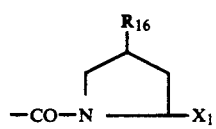

wherein
$R_7$ is hydrogen or $C_{1-3}$alkyl, $R_{10}$ is hydrogen or the residue of a physiologically acceptable, physiologically hydrolysable ester, $R_{11}$ is hydrogen, $C_{1-3}$alkyl, phenyl or $C_{7-10}$phenylalkyl, $R_{12}$ is hydrogen, $C_{1-3}$alkyl or a group of formula $-CH(R_{13})-X_1$, $R_{13}$ is $CH_2OH$, $-(CH_2)_2-OH$, $-(CH_2)_3-OH$, or $-CH(CH_3)OH$ or represents the substituent attached to the α-carbon atom of a natural or synthetic α-amino acid (including hydrogen) and $X_1$ is a group of formula $-COOR_7$, $-CH_2OR_{10}$ or $$-CO-N\begin{matrix}R_{14}\\R_{15}\end{matrix}$$

wherein $R_7$ and $R_{10}$ have the meanings given above, $R_{14}$ is hydrogen or $C_{1-3}$alkyl and $R_{15}$ is hydrogen, $C_{1-3}$alkyl, phenyl or $C_{7-10}$phenylalkyl, and $R_{16}$ is hydrogen or hydroxy, with the proviso that when $R_{12}$ is $-CH(R_{13})-X_1$ then $R_{11}$ is hydrogen or methyl, wherein the residues B, D and E have the L-configuration, and the residues in the 2-and 7-position and any residues $Y_1$ 4) and $Y_2$ 4) each independently have the (L)- or (D)-configuration, in free form or in pharmaceutically acceptable salt or complex form.

2. A method according to claim 1 for treating arthritic conditions or diseases.

3. A method according to claim 1 for treating rheumatoid arthritis.

4. A method according to claim 1 for treating osteoarthritis.

5. A method according to claim 1, wherein the somatostatin analogue is $$\overline{(D)Phe-Cys-Phe-(D)Trp-Lys-Thr-Cys}-Thr-ol,$$

in free form or in pharmaceutically acceptable salt or complex form.

6. A method according to claim 1, wherein the somatostatin analogue is $$\overline{(D)Phe-Cys-Tyr-(D)Trp-Lys-Val-Cys}-ThrNH_2,$$

in free form or in pharmaceutically acceptable salt or complex form.

7. A method according to claim 1, wherein the somatostatin analogue is $$\overline{(D)Phe-Cys-Tyr-(D)Trp-Lys-Val-Cys}-TrpNH_2,$$

in free form or in pharmaceutically acceptable salt or complex form.

8. A method according to claim 1, wherein the somatostatin analogue is

β-naphthyl- $$\overline{(D)Ala-Cys-Tyr-(D)Trp-Lys-Val-Cys}-Thr-NH_2,$$

in free form or in pharmaceutically acceptable salt or complex form.

9. A method according to claim 1, wherein the somatostatin analogue or derivative is a compound of formula IV bearing a sugar residue on the N-terminal amino group.

10. A method according to claim 1, wherein the somatostatin analogue or derivative bears a sugar residue selected from the group consisting of a residue $$G_1\diagdown\!\!\!\diagdown\!\!\!\begin{matrix}O\\\phantom{X}\\CH_2-\end{matrix}\!\!\!\diagup\!\!\!OH$$

which is a radical obtainable by means of an Amadori rearrangement from a natural or synthetically accessible mono-, di- or oligosaccharide, a residue $$G_2\diagdown\!\!\!\diagdown\!\!\!\begin{matrix}O\\\phantom{X}\\NH-\end{matrix}\!\!\!\diagup\!\!\!OH$$

which is a radical obtainable by means of a Heyns rearrangement from a natural or a synthetically accessible mono-, di-or oligoketose, and a residue $$G_4'\diagdown\!\!\!\diagdown\!\!\!\begin{matrix}O\\\phantom{X}\end{matrix}\!\!\!\diagup\!\!\!O-Q'-\quad\text{or of formula}$$

$$G_4\diagdown\!\!\!\diagdown\!\!\!\begin{matrix}O\\\phantom{X}\end{matrix}\!\!\!\diagup\!\!\!NH-Q-$$

which are each independently a sugar residue linked to the N-terminal amino group by a coupling group Q or Q'.

11. A method according to claim 10 wherein the somatostatin derivative or analogue is $N^\alpha$-[α-glucosyl(1-4)-deoxy-fructosyl]-

$$\overline{DPhe-Cys-Phe-DTrp-Lys-Thr-Cys}-Thr-ol,$$

in free form or in pharmaceutically acceptable salt or complex form.

* * * * *